(12) United States Patent
Medoff et al.

(10) Patent No.: US 9,677,043 B2
(45) Date of Patent: *Jun. 13, 2017

(54) BIOPROCESSING

(71) Applicant: XYLECO, INC., Woburn, MA (US)

(72) Inventors: Marshall Medoff, Brookline, MA (US); Thomas Craig Masterman, Rockport, MA (US)

(73) Assignee: XYLECO, INC., Wakefield, MA (US)

( * ) Notice: Subject to any disclaimer, the term of this patent is extended or adjusted under 35 U.S.C. 154(b) by 68 days.

This patent is subject to a terminal disclaimer.

(21) Appl. No.: 15/044,013

(22) Filed: Feb. 15, 2016

(65) Prior Publication Data

US 2016/0160171 A1 Jun. 9, 2016

Related U.S. Application Data

(63) Continuation of application No. 14/196,589, filed on Mar. 4, 2014, now Pat. No. 9,284,586, which is a (Continued)

(51) Int. Cl.
*C12M 1/00* (2006.01)
*C12M 1/36* (2006.01)
(Continued)

(52) U.S. Cl.
CPC ......... *C12M 41/48* (2013.01); *B01F 3/04106* (2013.01); *B01F 3/04539* (2013.01); *B01F 3/04609* (2013.01); *B01F 5/0212* (2013.01); *B01F 5/10* (2013.01); *C12M 27/00* (2013.01); *C12M 27/02* (2013.01); *C12M 29/00* (2013.01); *C12M 29/06* (2013.01); *C12M 29/12* (2013.01);
(Continued)

(58) Field of Classification Search
CPC ...... C12M 41/48; C12M 41/12; C12M 41/26; C12M 41/32; C12M 27/00; C12M 29/00; C12M 29/22
See application file for complete search history.

(56) References Cited

U.S. PATENT DOCUMENTS 4,176,522 A 12/1979 Holtzapple et al.
4,426,450 A 1/1984 Donofrio
(Continued)

FOREIGN PATENT DOCUMENTS

BE 414030 3/1936
CN 2110640 7/1992
(Continued)

*Primary Examiner* — Michael Hobbs
(74) *Attorney, Agent, or Firm* — Leber IP Law

(57) ABSTRACT

Bioreactors are disclosed that include a vessel, a jet mixing system comprising a plurality of jet flow agitators disposed in the vessel, each jet flow agitator comprising a shaft, a shroud surrounding the shaft, the shaft having a bore and a plurality of orifices in communication with the bore, and an impeller mounted on the shaft within the shroud, and a gas delivery system configured to supply a process gas to the vessel through the bore such that the gas exits the orifices. The vessel may include a vent, and the gas delivery system may include a source of oxygen in communication with the vessel, an oxygen monitor configured to monitor the oxygen content of a liquid in the vessel, and a controller configured to adjust the oxygen content of the liquid, using the vent and oxygen source, in response to input from the oxygen monitor.

16 Claims, 13 Drawing Sheets

Related U.S. Application Data continuation of application No. 13/293,977, filed on Nov. 10, 2011, now Pat. No. 8,669,099, which is a continuation of application No. PCT/US2010/035328, filed on May 18, 2010.

(60) Provisional application No. 61/179,995, filed on May 20, 2009, provisional application No. 61/218,832, filed on Jun. 19, 2009, provisional application No. 61/218,803, filed on Jun. 19, 2009.

(51) Int. Cl.

| | | |
|---|---|---|
| *B01F 3/04* | (2006.01) | |
| *B01F 5/02* | (2006.01) | |
| *B01F 5/10* | (2006.01) | |
| *C12M 1/06* | (2006.01) | |
| *C12M 1/21* | (2006.01) | |
| *C12M 1/34* | (2006.01) | |
| *C12P 19/02* | (2006.01) | |
| *C12P 19/14* | (2006.01) | |
| *C12M 1/02* | (2006.01) | |

(52) U.S. Cl.
CPC ............ *C12M 29/22* (2013.01); *C12M 41/02* (2013.01); *C12M 41/12* (2013.01); *C12M 41/26* (2013.01); *C12M 41/28* (2013.01); *C12M 41/32* (2013.01); *C12M 41/34* (2013.01); *C12P 19/02* (2013.01); *C12P 19/14* (2013.01); *B01F 2215/0463* (2013.01); *B01F 2215/0481* (2013.01)

(56) References Cited

U.S. PATENT DOCUMENTS

| | | |
|---|---|---|
| 5,779,996 A | 7/1998 | Stormo |
| 6,455,306 B1 | 9/2002 | Goldstein et al. |
| 8,669,099 B2 | 3/2014 | Medoff et al. |
| 2003/0211130 A1 | 11/2003 | Sanders et al. |
| 2004/0050764 A1 | 3/2004 | Perriello |
| 2007/0172945 A1 | 7/2007 | O'Kennedy et al. |
| 2008/0139865 A1 | 6/2008 | Galliher et al. |
| 2008/0193991 A1 | 8/2008 | Allen et al. |
| 2008/0202504 A1 | 8/2008 | Hilst |
| 2010/0093073 A1 | 4/2010 | Erhardt et al. |
| 2010/0162619 A1 | 7/2010 | Peus |

FOREIGN PATENT DOCUMENTS

| | | |
|---|---|---|
| CN | 2142464 | 9/1993 |
| CN | 2334762 | 8/1999 |
| CN | 2762897 | 3/2006 |
| CN | 1844347 | 10/2006 |
| DE | 2310256 | 9/1973 |
| DE | 102007062808 | 7/2008 |
| GB | 470898 | 8/1937 |
| JP | 1017701 | 1/1989 |
| JP | 2006121954 | 5/2006 |
| JP | 2009045037 | 3/2009 |

BIOPROCESSING

RELATED APPLICATIONS

This application is a continuation of U.S. Ser. No. 14/196,589, filed Mar. 4, 2014, now U.S. Pat. No. 9,284,586, granted Mar. 15, 2016, which is a continuation of U.S. Ser. No. 13/293,977, filed Nov. 10, 2011, now U.S. Pat. No. 8,669,099, granted Mar. 11, 2014, which is a continuation of PCT/US2010/035328, filed May 18, 2010, which claimed priority to U.S. Provisional Application Ser. No. 61/179,995, filed May 20, 2009, U.S. Provisional Application Ser. No. 61/218,832, filed Jun. 19, 2009, and U.S. Provisional Application Ser. No. 61/218,803, filed Jun. 19, 2009. The complete disclosure of each of these applications is hereby incorporated by reference herein.

BACKGROUND

Bioreactors, often referred to as fermentors, are commonly used in bioprocessing. "Bioprocessing" refers to aerobic and anaerobic processes that involve microorganisms, e.g., cells, in a medium. Examples of bioprocesses include yeast fermentation, bacterial fermentation, cell culture, bacterial culture, and the production of a product using cells, e.g., using mammalian cells such as CHO cells to express a protein, e.g., a therapeutic protein, or an enzyme.

A bioreactor generally includes a vessel in which a bioprocess is carried out, and sensors and process controls that allow parameters of the process to be monitored and controlled. Bioreactors also typically include an agitator, for example a Rushton or marine impeller, that mixes the vessel contents during bioprocessing.

It is generally important to carefully control process parameters during bioprocessing, for example gas flow rates, temperature, pH, dissolved oxygen level, and agitation speed and conditions. Dissolved oxygen level is a measure of oxygen transfer from gas to liquid phase, which is important to many bioprocesses and can be difficult to accomplish. While oxygen transfer is generally helped by agitation, agitation speed is often limited by power consumption and in some cases the risk of damage to the microorganisms. In some cases, for example, in the case of mammalian cells, the microorganisms are fragile and may be sensitive to heat, shear, and/or other process conditions.

SUMMARY

Generally, this invention relates to bioreactors, and to bioprocessing methods using bioreactors.

Bioprocessing can be enhanced by the use of certain mixing techniques and equipment, which may enhance the reaction rate and improve the efficiency of the process. The mixing techniques and equipment disclosed herein also enhance mass tranfer, and as a result reaction rates in a mixture, and avoid or minimize harm to sensitive ingredients of the mixture such as microorganisms and enzymes. In particular, jet mixing techniques, including for example jet aeration and jet flow agitation, have been found to provide good wetting, dispersion and mechanical disruption. The mixing techniques and equipment disclosed herein can in some cases allow the solids level of the mixture being processed to be increased, and thus the process can proceed more rapidly, more efficiently and more cost-effectively, and the resulting concentration of the final product can be increased. The mixing systems described herein generally do not impart high shear to the liquid. In some implementations, the mixing systems do not cause a deleterious increase in the overall temperature of the liquid. As a result, microorganisms and cells used in bioprocessing are maintained in a viable condition throughout the process.

In one aspect, the invention features a bioreactor that includes a vessel and a jet mixer disposed in the vessel. In another aspect, the invention features a method that includes placing a microorganism or cells and a fluid medium in a vessel, and mixing the contents of the vessel by operation of a jet mixer.

Some embodiments include one or more of the following features. The bioreactor can further include sensors and process controllers. For example, the bioreactor can further include a temperature control system configured to regulate the temperature in the vessel. The bioreactor can include a gas delivery system configured to supply a process gas, e.g., air, oxygen, nitrogen or carbon dioxide, to the vessel. In some cases the vessel includes a vent, and the bioreactor includes a source of oxygen in communication with the vessel, an oxygen monitor configured to monitor the oxygen content of a liquid in the vessel, an a controller configured to adjust the oxygen content of the liquid, using the vent and oxygen source, in response to input from the oxygen monitor. The flow rate of oxygen into the vessel, if oxygenation is required, can be relatively low. For example, the controller may be configured to oxygenate the vessel at a rate of less than 0.2 vvm, e.g., less than 0.1, 0.05, 0.025, or even less than 0.01 vvm.

The bioreactor may further include a concentration monitor configured to monitor the concentration of a product in the liquid in the vessel, and a controller configured to stop the bioprocess based on input received from the concentration monitor. In some cases, the system includes a process-terminating module configured to stop the bioprocess in response to a signal received from the controller.

The jet mixer may include, for example, a jet-flow agitator, a jet aeration type mixer, or a suction chamber jet mixer. If a jet aeration type mixer is used, it may be used with or without injection of air through the mixer. For example, if the jet aeration type mixer includes a nozzle having a first inlet line and a second inlet line, in some cases both inlet lines are supplied with a liquid.

The bioreactor may include delivery devices configured to deliver the medium, microorganisms or cells, and/or any other materials used in the bioprocess, such as buffers, foam control agents, and the like, to the vessel. The bioreactor may include an outlet through which effluent can be collected. The jet mixer can further include a motor, and the bioreactor can further include a device configured to monitor the torque on the motor during mixing and adjust the operation of the delivery devices and/or the outlet, and/or the torque of the motor, based on input from the torque-monitoring device. In addition, or alternatively, the bioreactor may include an amp monitoring device, configured to measure the full-load amperage of the motor. The bioreactor may also include a variable frequency drive (VFD) configured to adjust the speed of the motor.

In some embodiments, the mixer is configured to limit any increase in the overall temperature of a fluid medium in the vessel to less than 5 degrees C. over the course of mixing.

In another aspect, the invention features a bioreactor that includes a mixer that produces generally toroidal flow within the vessel. The invention also features methods of bioprocessing using the bioreactor. These aspects of the invention may include, in some embodiments, any one or more of the features discussed above.

Examples of products that can be produced by employing the bioreactors and methods described herein include hydrocarbons; proteins (e.g., therapeutic proteins); enzymes (e.g., cellulolytic enzymes); alcohols (e.g., monohydric alcohols or dihydric alcohols, such as ethanol, n-propanol or n-butanol); xylitol; carboxylic acids, such as acetic acid or butyric acid; salts and esters of carboxylic acids; mixtures of carboxylic acids with salts and/or esters of carboxylic acids (e.g., methyl, ethyl and n-propyl esters); ketones (e.g., acetone); aldehydes (e.g., acetaldehyde); alpha and beta unsaturated acids, such as acrylic acid; and olefins, such as ethylene. Specific examples include ethanol, propanol, propylene glycol, butanol, 1,4-butanediol, 1,3-propanediol, methyl or ethyl esters of any of these alcohols, methyl acrylate, methylmethacrylate, lactic acid, proprionic acid, butyric acid, succinic acid, 3-hydroxypropionic acid, salts of any of these acids, and mixtures of any of these acids and their respective salts. These and other products are described in U.S. Ser. No. 12/417,900, the disclosure of which is incorporated by reference herein.

All publications, patent applications, patents, and other references mentioned herein or attached hereto are incorporated by reference in their entirety for all that they contain.

DETAILED DESCRIPTION

Figure 1:
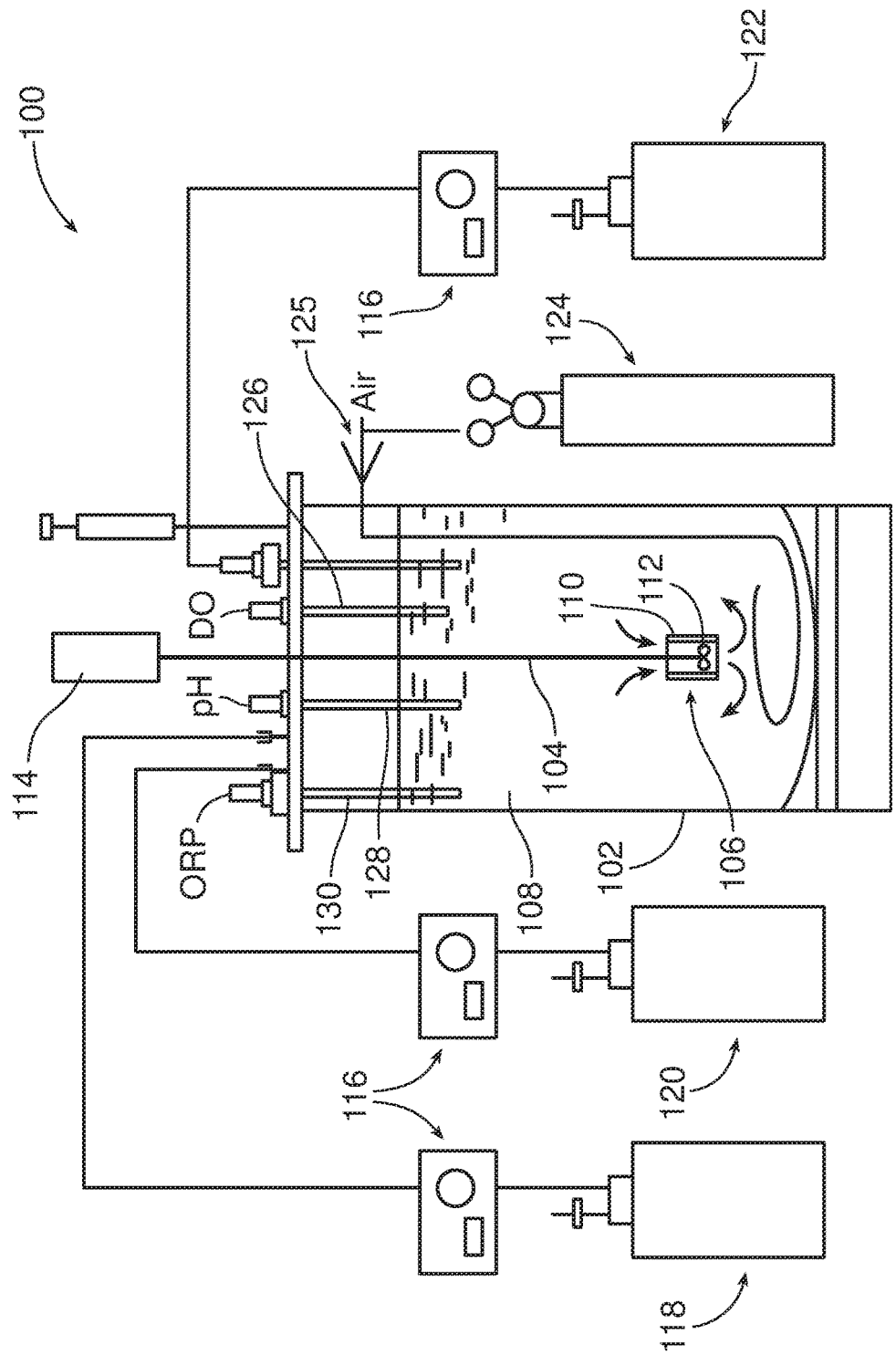
FIG. 1 is a diagram of a bioreactor according to one embodiment.

Referring to FIG. 1, a bioreactor 100 includes a vessel 102 in which a bioprocess takes place. Vessel 102 is generally of an autoclavable, inert material such as glass or stainless steel, and may or may not be jacketed. In some cases, the vessel may be relatively low volume, e.g., less than about 30,000 L. In other cases, the vessel may be relatively high volume, e.g., greater than 30,000 L, such as from about 50,000 L to 2 million liters, or even greater than 2 million liters. Suitable low volume vessels may have a total capacity, for example, of from about 5 L to 30,000 L, e.g., 50 L to 5000 L. For example, the total capacity of the vessel may be 75 L, 150 L, 300 L, 500 L, 1000 L, 1500 L, 3000 L, or 5000 L. It may be preferred that the vessel have an aspect ratio (diameter:height) of, for example, about 0.5:1 to about 4:1, or about 0.5:1 to 2:1, e.g., about 0.5:1 to 1:1.

A shaft 104 extends into the vessel, and a jet mixing device 106 is mounted at the distal end of the shaft. As will be discussed in detail below, the jet mixing device 106 creates a circulating flow in the liquid 108 in the vessel, as indicated by the arrows entering and leaving the jet mixing device. In the embodiment shown in FIG. 1, the jet mixing device 106 includes a shroud 110 and an impeller 112 disposed within the shroud. However, the jet mixer may have any of the structures disclosed herein, or any other desired structure which produces jet flow. In the embodiment shown in FIG. 1, the shaft 104 is driven by a motor 114. However, other types of jet systems may be used as will be discussed below.

The bioreactor may include any other desired bioreactor components and features. For example, as shown in FIG. 1, bioreactor 100 includes pumps 116, a container 118 for base solution, a container 120 for feed medium, a collection reservoir 122, and a source of gas 124 (multiple gas sources and appropriate valving and mixing may be included if desired). Air flow control is provided by a thermal mass flow controller 125. The bioreactor 100 also includes a dissolved oxygen probe 126, a pH probe 128, and a redox (ORP) probe 130 for monitoring these parameters, and a sampling probe 131 for sampling or harvesting the vessel contents. A condenser 132 is provided for condensation of volatiles.

The bioreactor generally includes a controller (not shown) that is configured to control the process parameters by receiving signals from various monitoring devices (e.g., the probes shown in FIG. 1) and adjusting the process parameters based on this data. For example, in bioreactor 100 the controller is configured to receive signals from the oxygen probe 126, pH probe 128, and redox probe 130, and control the input of gas, base solution, and feed solution, respectively, based on these signals. The controller may be, for example, a programmable logic controller (PLC) with an operator interface. The controller may optionally be configured to control multiple vessels.

In some implementations, gas delivery is through the shaft of the jet mixing device. For example, the shaft 104 may include a bore through which gas is delivered, and one or more orifices through which gas exits into the vessel. The orifices may be within the shroud 110, to enhance mixing, and/or at other locations along the length of shaft 104.

The bioreactor may also include a number of other features to enhance bioprocessing. For example, the vessel may be cooled, e.g., with a water jacket or other cooling system, to maintain a desired process temperature. A foam detector may be provided, and an anti-foam delivery system may be included to deliver an anti-foam agent to the vessel should excessive foaming occur. In some implementations, the bioreactor is sterilizable in place, e.g., with an automatic steam injection system. Various access ports may be provided in the vessel.

Mixing Characteristics

Various types of mixing devices are described below, and other mixing devices may be used. Suitable mixers have in common that they produce high velocity circulating flow, for example flow in a toroidal or elliptical pattern. Generally, preferred mixers exhibit a high bulk flow rate. Preferred mixers provide this mixing action with relatively low energy consumption. It is also generally preferred that the mixer produce relatively low shear and avoid heating of the liquid medium, as shear and/or heat can deleteriously affect the microorganism or cells. As will be discussed in detail below, some preferred mixers draw the mixture through an inlet into a mixing element, which may include a rotor or impeller, and then expel the mixture from the mixing element through an outlet nozzle. This circulating action, and the high velocity of the jet exiting the nozzle, assist in dispersing material that is floating on the surface of the liquid or material that has settled to the bottom of the vessel, depending on the orientation of the mixing element. Mixing elements can be positioned in different orientations to disperse both floating and settling material, and the orientation of the mixing elements can in some cases be adjustable.

For example, in some preferred mixing systems the velocity $v_o$ of the jet as it meets the ambient fluid is from about 2 to 300 m/s, e.g., about 5 to 150 m/s or about 10 to 100 m/s. The power consumption of the mixing system may be about 20 to 1000 KW, e.g., 30 to 570 KW, 50 to 500 KW, or 150 to 250 KW for a 100,000 L tank. It is generally preferred that the power usage be low for cost-effectiveness.

Jet Mixing

Figure 11:
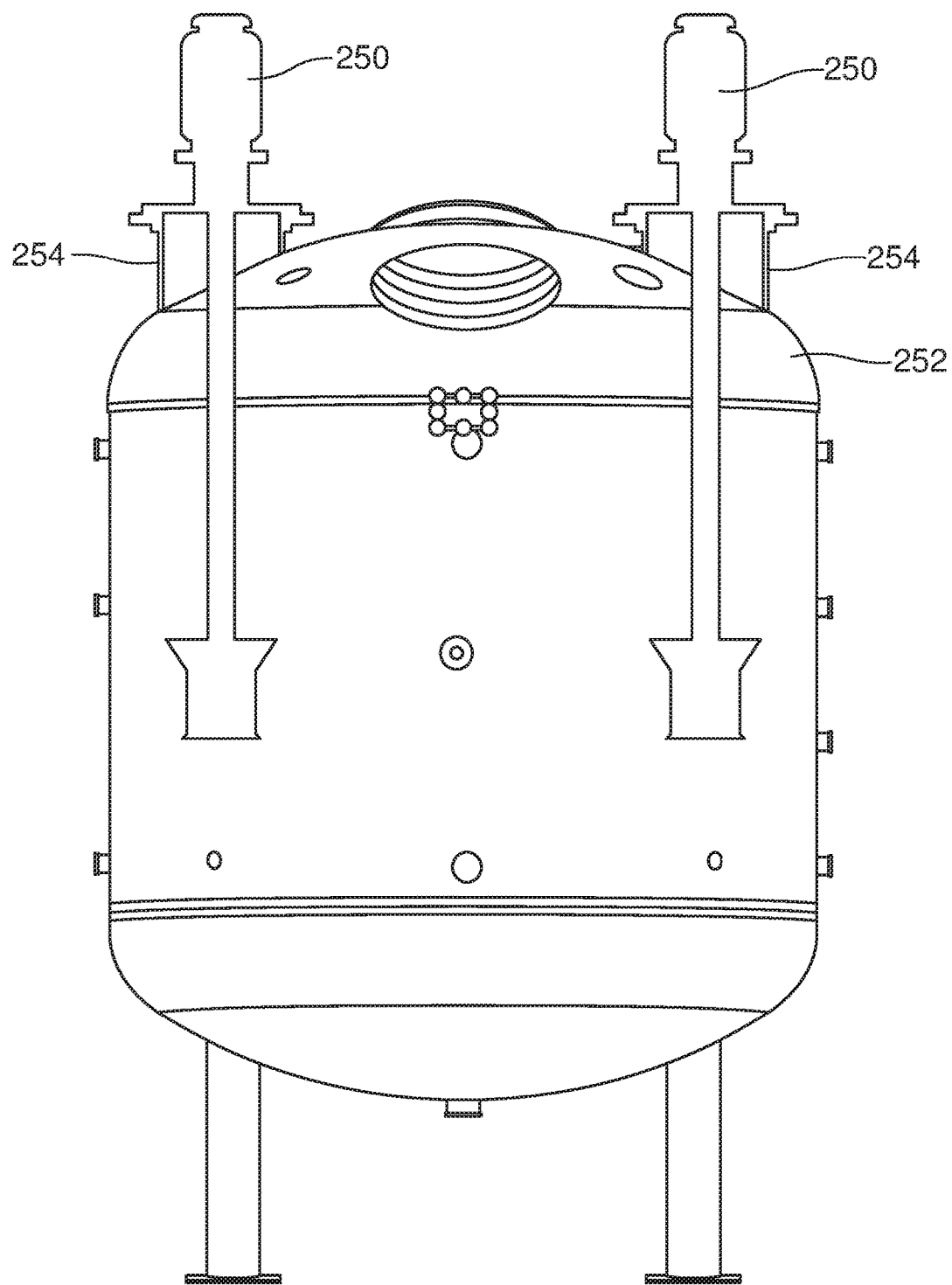
FIG. 11 is a cross-sectional view of a vessel having a domed bottom and two jet mixers extending into the vessel from above.

Jet mixing involves the discharge of a submerged jet, or a number of submerged jets, of high velocity liquid into a fluid medium, in this case the mixture in the vessel of the bioreactor. The jet of liquid penetrates the fluid medium, with its energy being dissipated by turbulence and some initial heat. This turbulence is associated with velocity gradients (fluid shear). The surrounding fluid is accelerated and entrained into the jet flow, with this secondary entrained flow increasing as the distance from the jet nozzle increases. The momentum of the secondary flow remains generally constant as the jet expands, as long as the flow does not hit a wall, floor or other obstacle. The longer the flow continues before it hits any obstacle, the more liquid is entrained into the secondary flow, increasing the bulk flow in the vessel. When it encounters an obstacle, the secondary flow will lose momentum, more or less depending on the geometry of the vessel, e.g., the angle at which the flow impinges on the obstacle. It is generally desirable to orient the jets and/or design the vessel so that hydraulic losses to the vessel walls are minimized. For example, it may be desirable for the vessel to have an arcuate bottom (e.g., a domed headplate), and for the jet mixers to be oriented relatively close to the sidewalls, as shown in FIG. 11. The vessel bottom may have any desired domed configuration, or may have an elliptical or conical geometry.

Jet mixing differs from most types of liquid/liquid and liquid/solid mixing in that the driving force is hydraulic rather than mechanical. Instead of shearing fluid and propelling it around the mixing vessel, as a mechanical agitator does, a jet mixer forces fluid through one or more nozzles within the vessel, creating high-velocity jets that entrain other fluid. The result is shear (fluid against fluid) and circulation, which mix the vessel contents efficiently.

Figure 2:
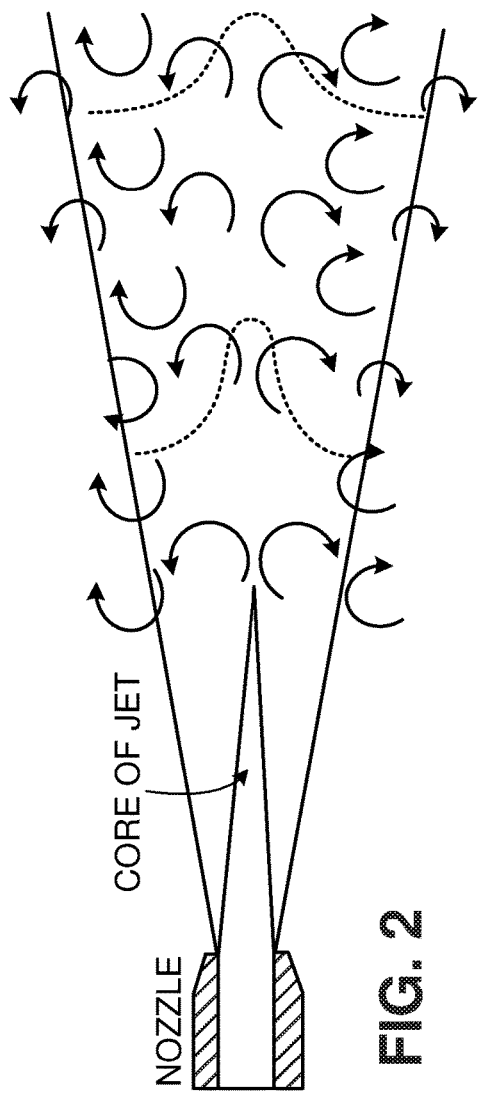
FIGS. 2 and 2A are diagrams illustrating jet flow exiting a nozzle.
Figure 2A:
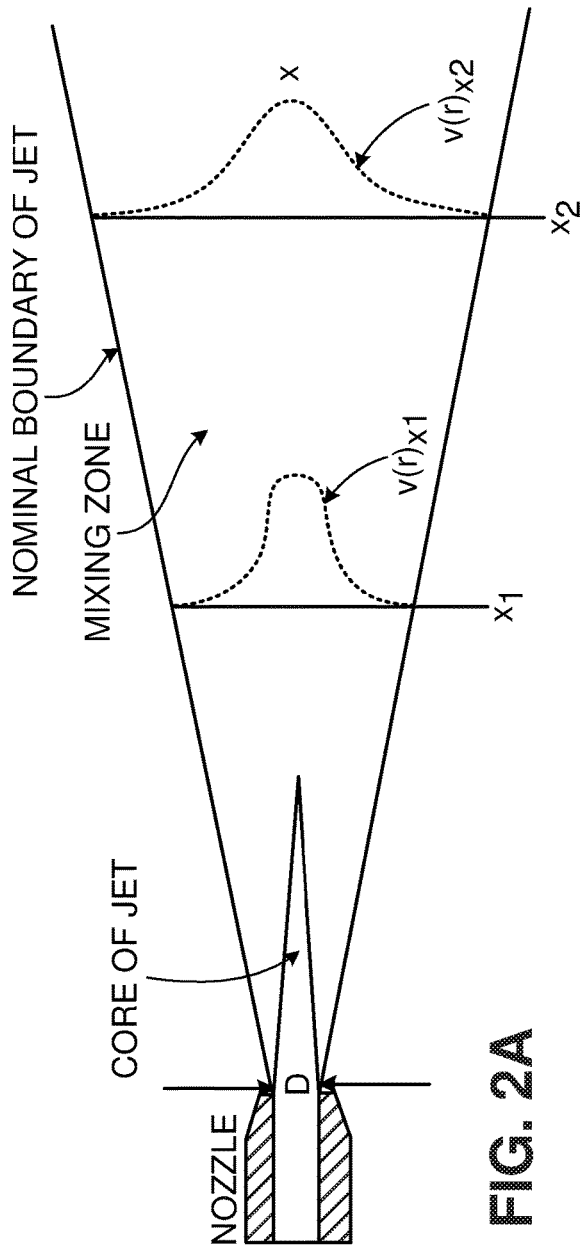

Referring to FIG. 2, the high velocity gradient between the core flow from a submerged jet and the surrounding fluid causes eddies. FIG. 2A illustrates the general characteristics of a submerged jet. As the submerged jet expands into the surrounding ambient environment the velocity profile flattens as the distance (x) from the nozzle increases. Also, the velocity gradient dv/dr changes with r (the distance from the centerline of the jet) at a given distance x, such that eddies are created which define the mixing zone (the conical expansion from the nozzle).

In an experimental study of a submerged jet in air (the results of which are applicable to any fluid, including water), Albertson et al. ("Diffusion of Submerged Jets," Paper 2409, Amer. Soc. of Civil Engineers Transactions, Vol. 115:639-697, 1950, at p. 657) developed dimensionless relationships for $v(x)_{r=0}/v_o$ (centerline velocity), $v(r)_x/v(x)_{r=0}$ (velocity profile at a given x), $Q_x/Q_o$ (flow entrainment), and $E_x/E_o$ (energy change with x):

(1) Centerline velocity, $v(x)_{r=0}/v_o$:

$$\frac{v(r=0)}{v_o} \frac{x}{D_o} = 6.2$$

(2) velocity profile at any x, $v(r)_x/v(x)_{r=0}$:

$$\log\left[\frac{v(r)_x}{v_o} \frac{x}{D}\right] = 0.79 - 33\frac{r^2}{x^2}$$

(3) Flow and energy at any x:

$$\frac{Q_x}{Q_o} = 0.32\frac{x}{D_o} \qquad (10.21)$$

$$\frac{E_x}{E_o} = 4.1\frac{D_o}{x} \qquad (10.22)$$

where:
v(r=0)=centerline velocity of submerged jet (m/s),
$v_o$=velocity of jet as it emerges from the nozzle (m/s),
x=distance from nozzle (m),
r=distance from centerline of jet (m),
$D_o$=diameter of nozzle (m),
$Q_x$=flow of fluid across any given plane at distance x from the nozzle (me/s),
$Q_o$=flow of fluid emerging from the nozzle (m3/s),
E=energy flux of fluid across any given plane at distance x from the nozzle ($m^3$/s),
$E_o$=energy flux of fluid emerging from the nozzle ($m^3$/s).
("Water Treatment Unit Processes: Physical and Chemical," David W. Hendricks, CRC Press 2006, p. 411.)

Jet mixing is particularly cost-effective in large-volume (over 1,000 gal) and low-viscosity (under 1,000 cPs) applications. It is also generally advantageous that in most cases the pump or motor of the jet mixer not be submerged, e.g., when a pump is used it is generally located outside the vessel.

One advantage of jet mixing is that the temperature of the ambient fluid (other than directly adjacent the exit of the nozzle, where there may be some localized heating) is increased only slightly if at all. For example, the temperature may be increased by less than 5° C., less than 1° C., or not to any measureable extent.

Jet-Flow Agitators

Figure 3:
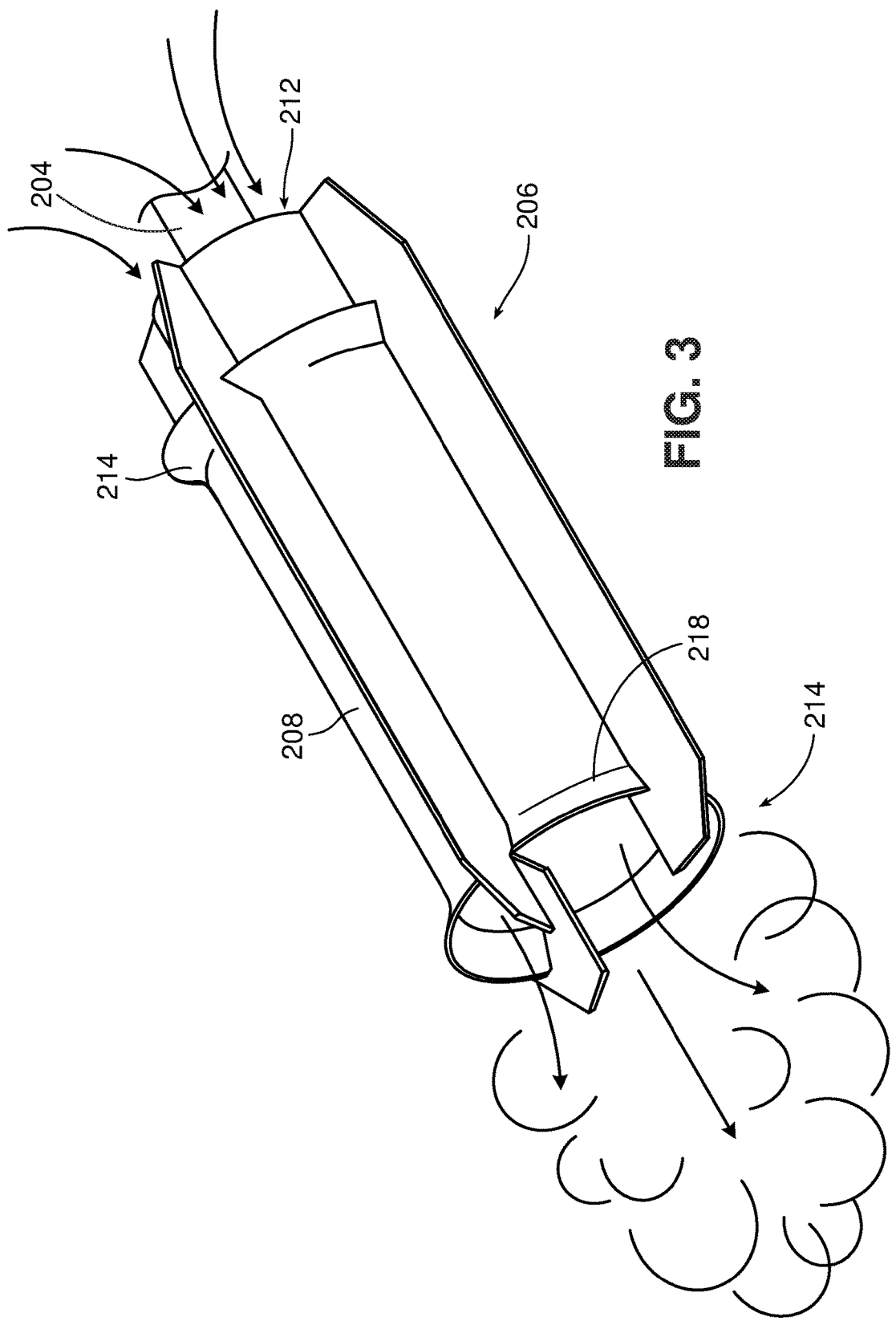
FIG. 3 is a diagrammatic perspective view of a jet-flow agitator according to one embodiment.
Figure 3A:
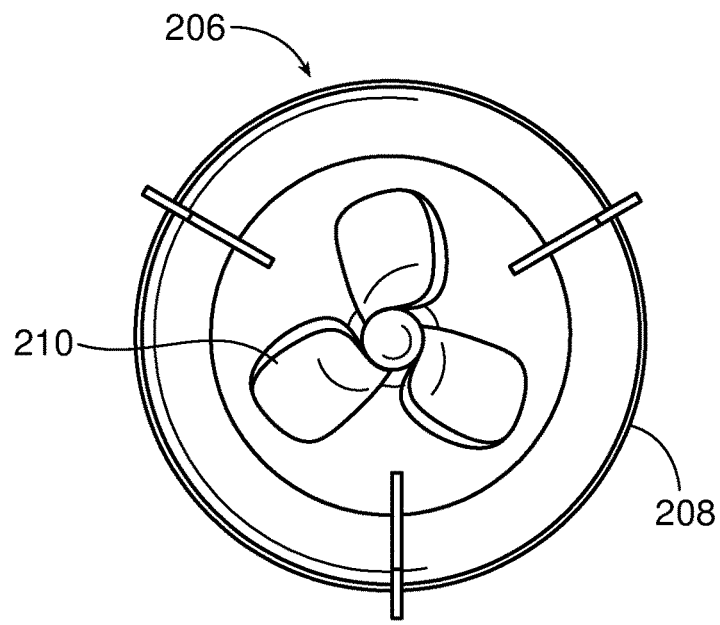
FIG. 3A is an enlarged perspective view of the impeller and jet tube of the jet-flow agitator of FIG. 3.

One type of jet-flow agitator is shown in FIGS. 3-3A. This type of mixer is available commercially, e.g., from IKA under the tradename ROTOTRON™. Referring to FIG. 3, the mixer 200 includes a motor 202, which rotates a drive shaft 204. A mixing element 206 is mounted at the end of the drive shaft 204. As shown in FIG. 3A, the mixing element 206 includes a shroud 208 and, within the shroud, an impeller 210. As indicated by the arrows, when the impeller is rotated in its "forward" direction, the impeller 210 draws liquid in through the open upper end 212 of the shroud and forces the liquid out through the open lower end 214. Liquid exiting end 214 is in the form of a high velocity stream or jet. If the direction of rotation of the impeller 210 is reversed, liquid can be drawn in through the lower end 214 and ejected through the upper end 212. This can be used, for example, to suck in solids that are floating near or on the surface of the liquid in a vessel. (It is noted that "upper" and "lower" refer to the orientation of the mixer in FIG. 3; the mixer may be oriented in a vessel so that the upper end is below the lower end.)

The shroud 208 includes flared areas 216 and 218 adjacent its ends. These flared areas are believed to contribute to the generally toroidal flow that is observed with this type of mixer. The geometry of the shroud and impeller also concentrate the flow into a high velocity stream using relatively low power consumption.

Preferably, the clearance between the shroud 208 and the impeller 210 is sufficient so as to avoid excessive milling of the material as it passes through the shroud. For example, the clearance may be at least 10 times the average particle size of the solids in the mixture, preferably at least 100 times.

Figure 3B:
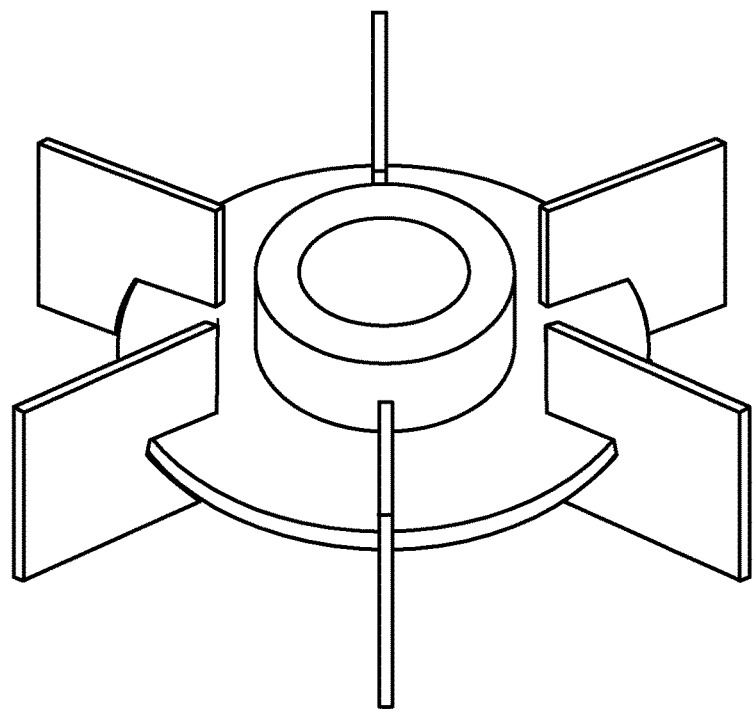
FIG. 3B is an enlarged perspective view of an alternate impeller.
Figure 3C:
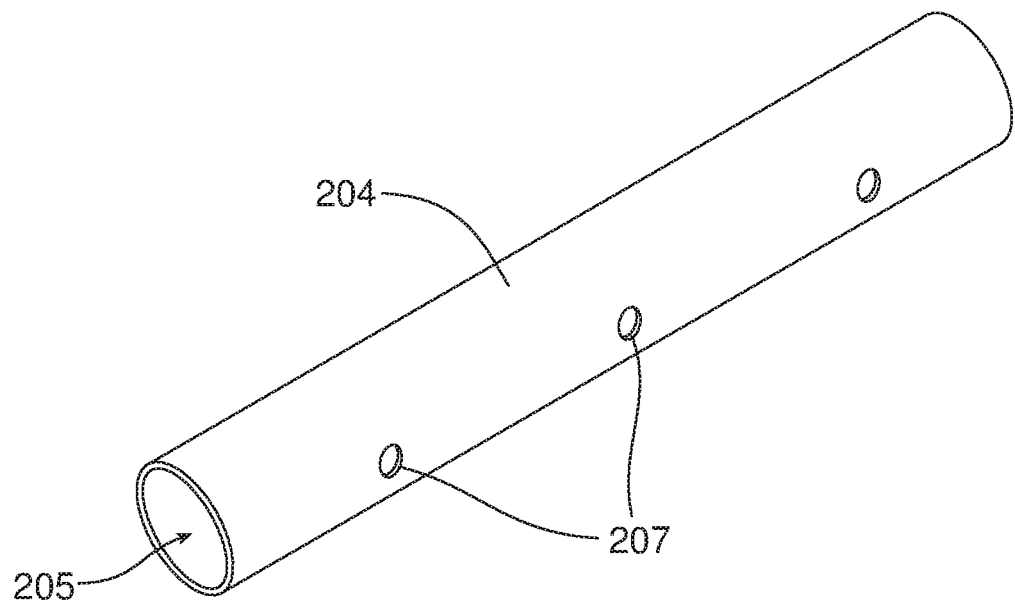
FIG. 3C is a diagrammatic view of a jet-flow agitator shaft having a plurality of orifices.

In some implementations, the shaft 204 is configured to allow gas delivery through the shaft. For example, as shown in FIG. 3C, the shaft 204 may include a bore 205 through which gas is delivered, and one or more orifices 207 through which gas exits into the mixture. The orifices may be within the shroud 208, to enhance mixing, and/or at other locations along the length of the shaft 204.

The impeller 210 may have any desired geometry that will draw liquid through the shroud at a high velocity. The impeller is preferably a marine impeller, as shown in FIG. 3A, but may have a different design, for example, a Rushton impeller as shown in FIG. 3B, or a modified Rushton impeller, e.g., tilted so as to provide some axial flow.

In order to generate the high velocity flow through the shroud, the motor 202 is preferably a high speed, high torque motor, e.g., capable of operating at 500 to 20,000 RPM, e.g., 3,000 to 10,000 RPM. However, the larger the mixer (e.g., the larger the shroud and/or the larger the motor) the lower the rotational speed can be. Thus, if a large mixer is used, such as a 5 hp, 10 hp, 20 hp, or 30 hp or greater, the motor may be designed to operate at lower rotational speeds, e.g., less than 2000 RPM, less than 1500 RPM, or even 500 RPM or less. The torque of the motor is preferably self-adjusting, to maintain a relatively constant impeller speed as the mixing conditions change over time.

Advantageously, the mixer can be oriented at any desired angle or location in the vessel, to direct the jet flow in a desired direction. Moreover, as discussed above, depending on the direction of rotation of the impeller the mixer can be used to draw fluid from either end of the shroud.

In some implementations, two or more jet mixers are positioned in the vessel, with one or more being configured to jet fluid upward ("up pump") and one or more being configured to jet fluid downward ("down pump"). In some cases, an up pumping mixer will be positioned adjacent a down pumping mixer, to enhance the turbulent flow created by the mixers. If desired, one or more mixers may be switched between upward flow and downward flow during processing. It may be advantageous to switch all or most of the mixers to up pumping mode to disperse material at the liquid surface, as up pumping creates significant turbulence at the surface.

Suction Chamber Jet Mixers

Another type of jet mixer includes a primary nozzle that delivers a pressurized fluid from a pump, a suction inlet adjacent the primary nozzle through which ambient fluid is drawn by the pressure drop between the primary nozzle and the wider inlet, and a suction chamber extending between the suction inlet and a secondary nozzle. A jet of high velocity fluid exits the secondary nozzle.

Figure 4:
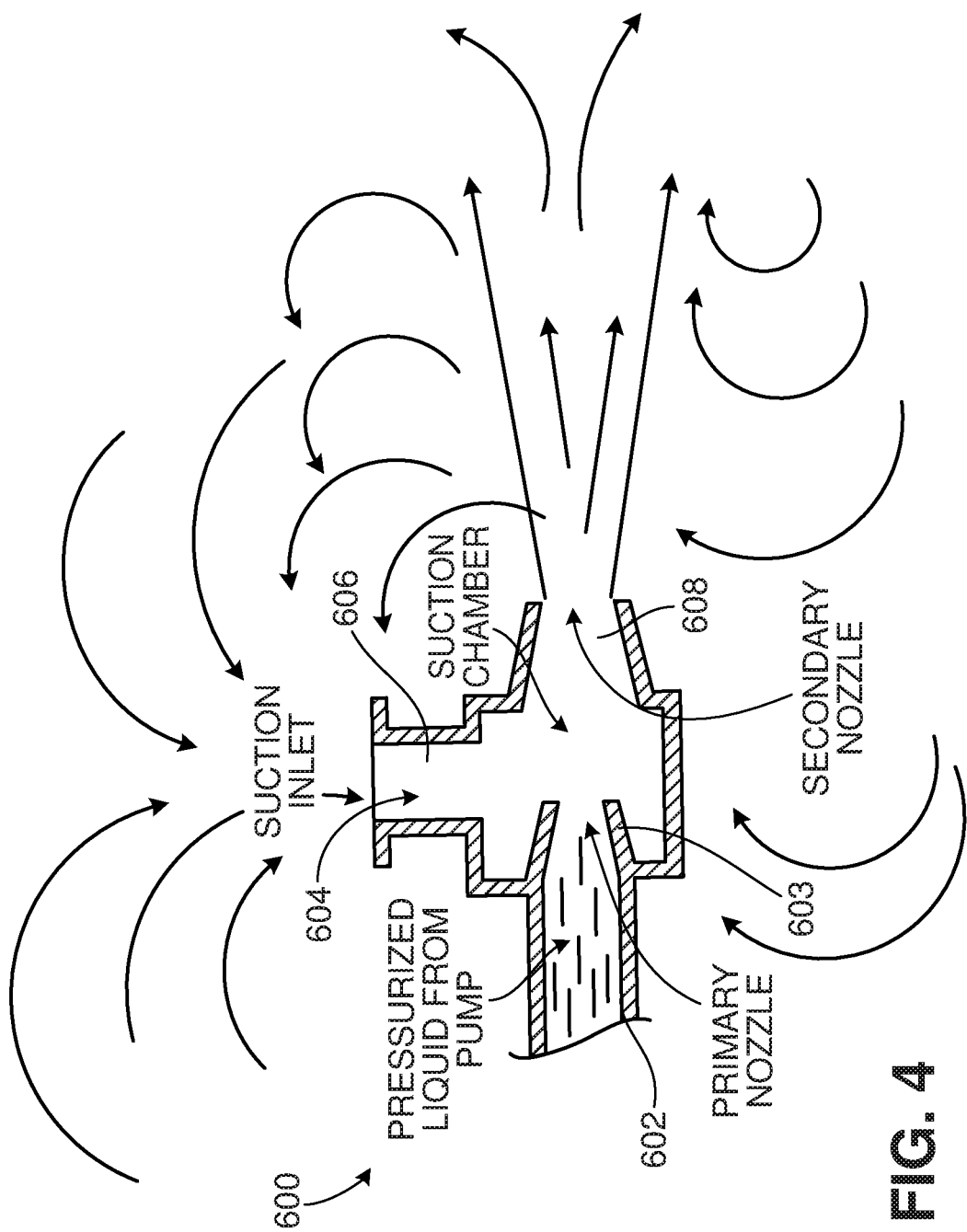
FIG. 4 is a diagram of a suction chamber jet mixing nozzle according to one embodiment.

An example of this type of mixer is shown in FIG. 4. As shown, in mixer 600 pressurized liquid from a pump (not shown) flows through an inlet passage 602 and exits through a primary nozzle 603. Ambient liquid is drawn through a suction inlet 604 into suction chamber 606 by the pressure drop caused by the flow of pressurized liquid. The combined flow exits from the suction chamber into the ambient liquid at high velocity through secondary nozzle 608. Mixing occurs both in the suction chamber and in the ambient liquid due to the jet action of the exiting jet of liquid.

Figure 5:
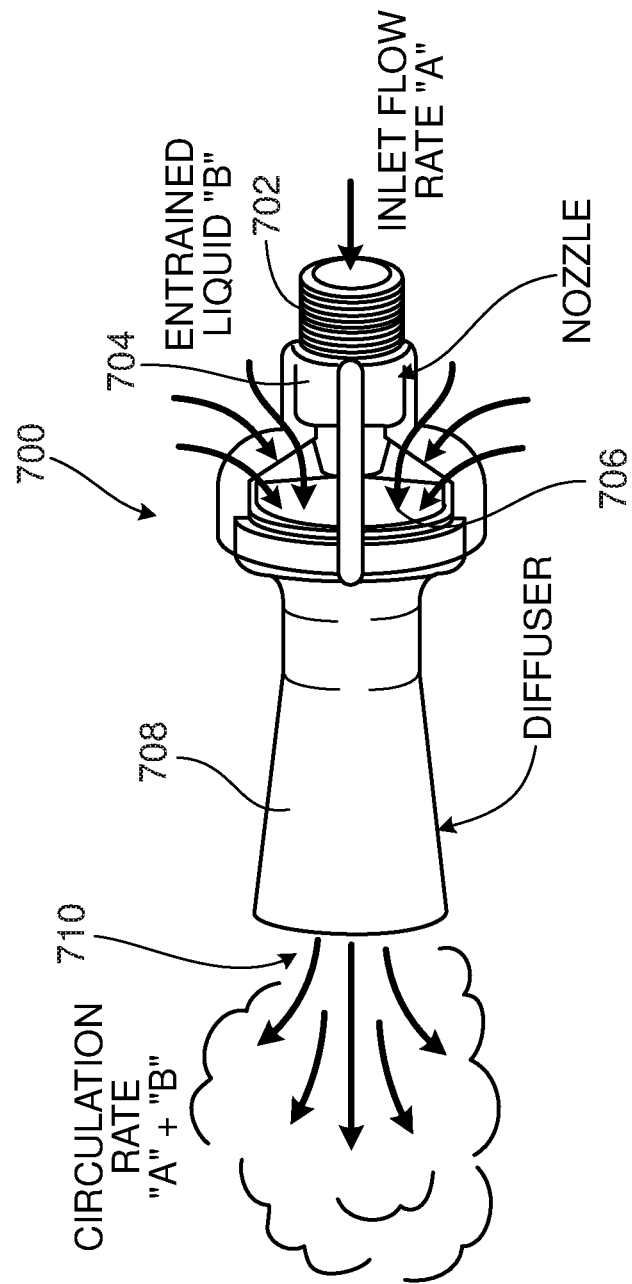
FIG. 5 is a diagrammatic perspective view of a jet mixing nozzle for a suction chamber jet mixing system according to another embodiment.
Figure 6:
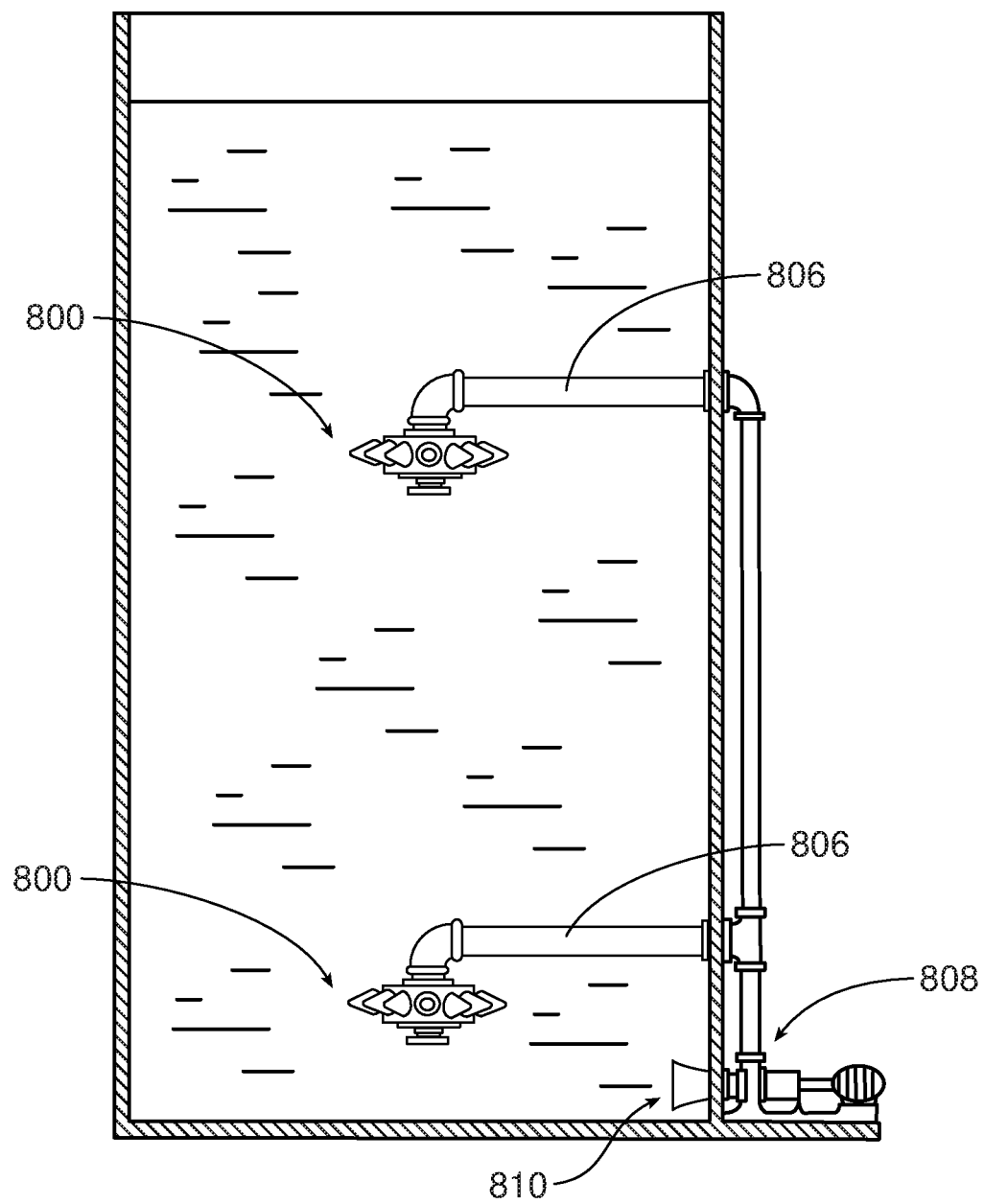
FIG. 6 is a side view of a bioreactor including a jet aeration type system according to one embodiment, showing a multi-level arrangement of nozzles in a vessel.

The nozzle shown in FIG. 5, referred to as an eductor nozzle, operates under a similar principle. A nozzle embodying this design is commercially available under the tradename TeeJet®. As shown, in nozzle 700 pressurized liquid flows in through an inlet 702 and exits a primary nozzle 704, drawing ambient fluid in to the open end 706 of a diffuser 708. The combined flow exits the opposite open end 710 of the diffuser at a circulation flow rate A+B that is the sum of the inlet flow rate A and the flow rate B of the entrained ambient fluid.

Jet Aeration Type Mixers

Another type of jet mixing system that can be utilized is referred to in the wastewater industry as "jet aeration mixing." In the wastewater industry, these mixers are typically used to deliver a jet of a pressurized air and liquid mixture, to provide aeration. However, in the present application in some cases the jet aeration type mixers are utilized without pressurized gas, as will be discussed below. The principles of operation of jet aeration mixers will be initially described in the context of their use with pressurized gas, for clarity.

Figure 7:
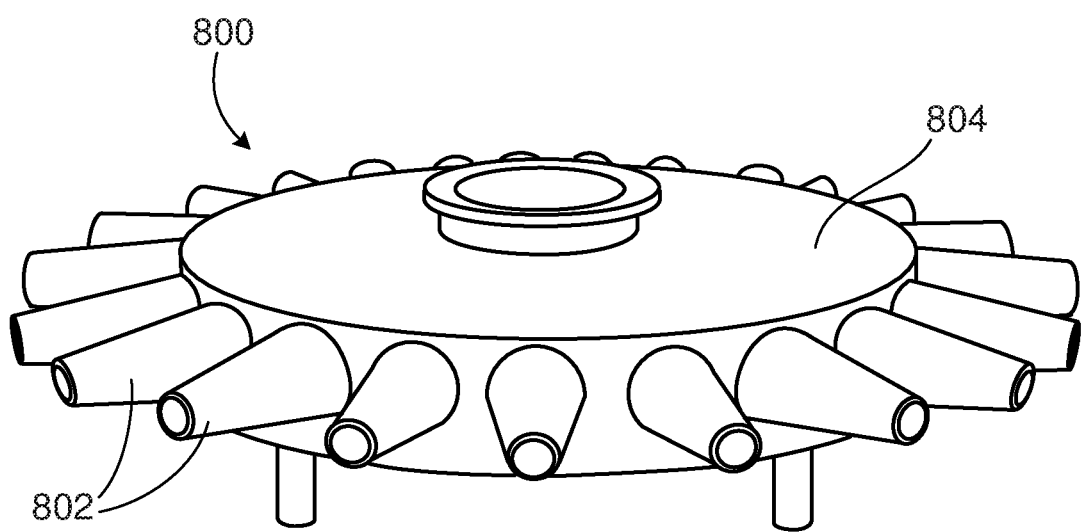
FIG. 7 is a perspective view of a jet aeration mixer according to one embodiment.

An eddy jet mixer, such as the mixer 800 shown in FIG. 7, includes multiple jets 802 mounted in a radial pattern on a central hub 804. The radial pattern of the jets uniformly distributes mixing energy throughout the vessel. The eddy jet mixer may be centrally positioned in a vessel, as shown, to provide toroidal flow about the center axis of the vessel. The eddy jet mixer may be mounted on piping 806, which supplies high velocity liquid to the eddy jet mixer. In some implementations air is also supplied to the eddy jet mixer. The high velocity liquid is delivered by a pump 808 which is positioned outside of the vessel and which draws liquid in through an inlet 810 in the side wall of the vessel.

Figure 8:
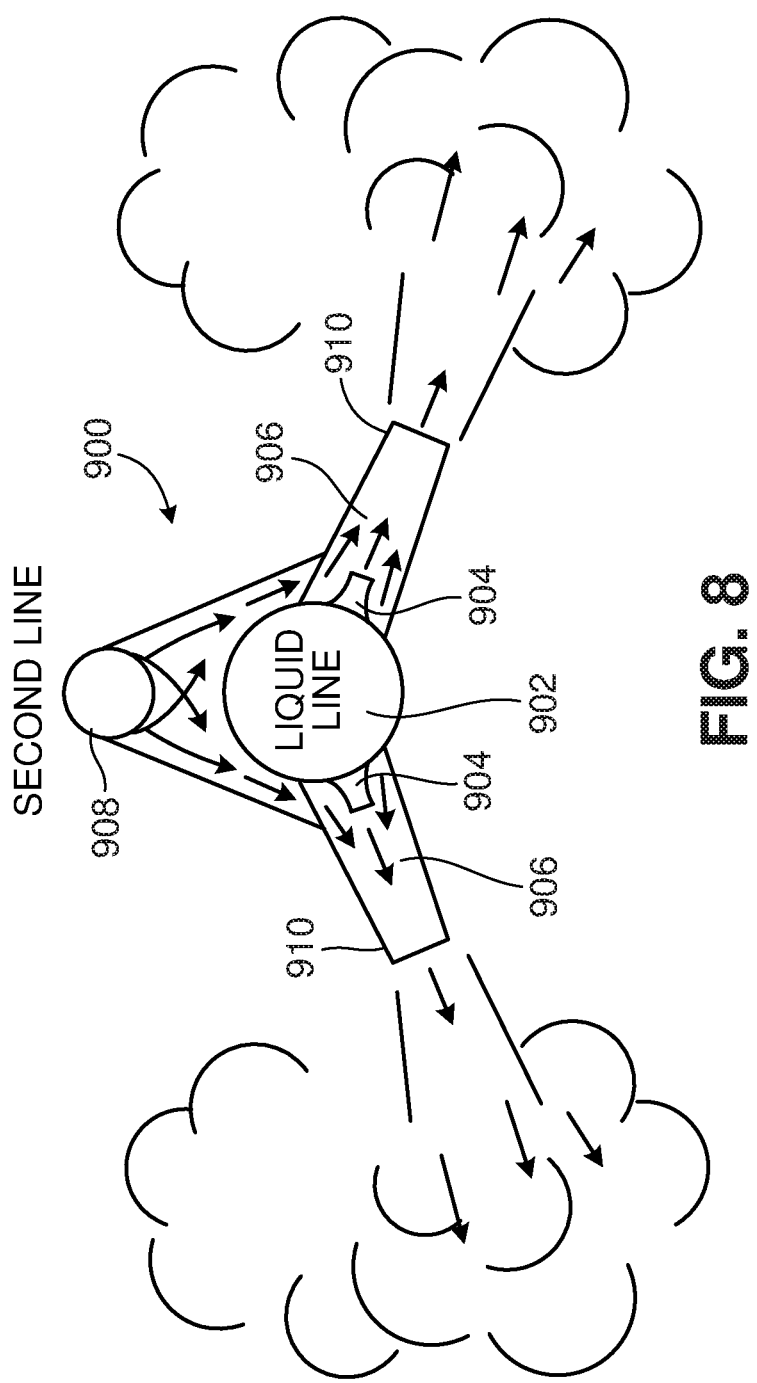
FIG. 8 is a cross-sectional view of a jet aeration type mixer according to one embodiment.
Figure 9:
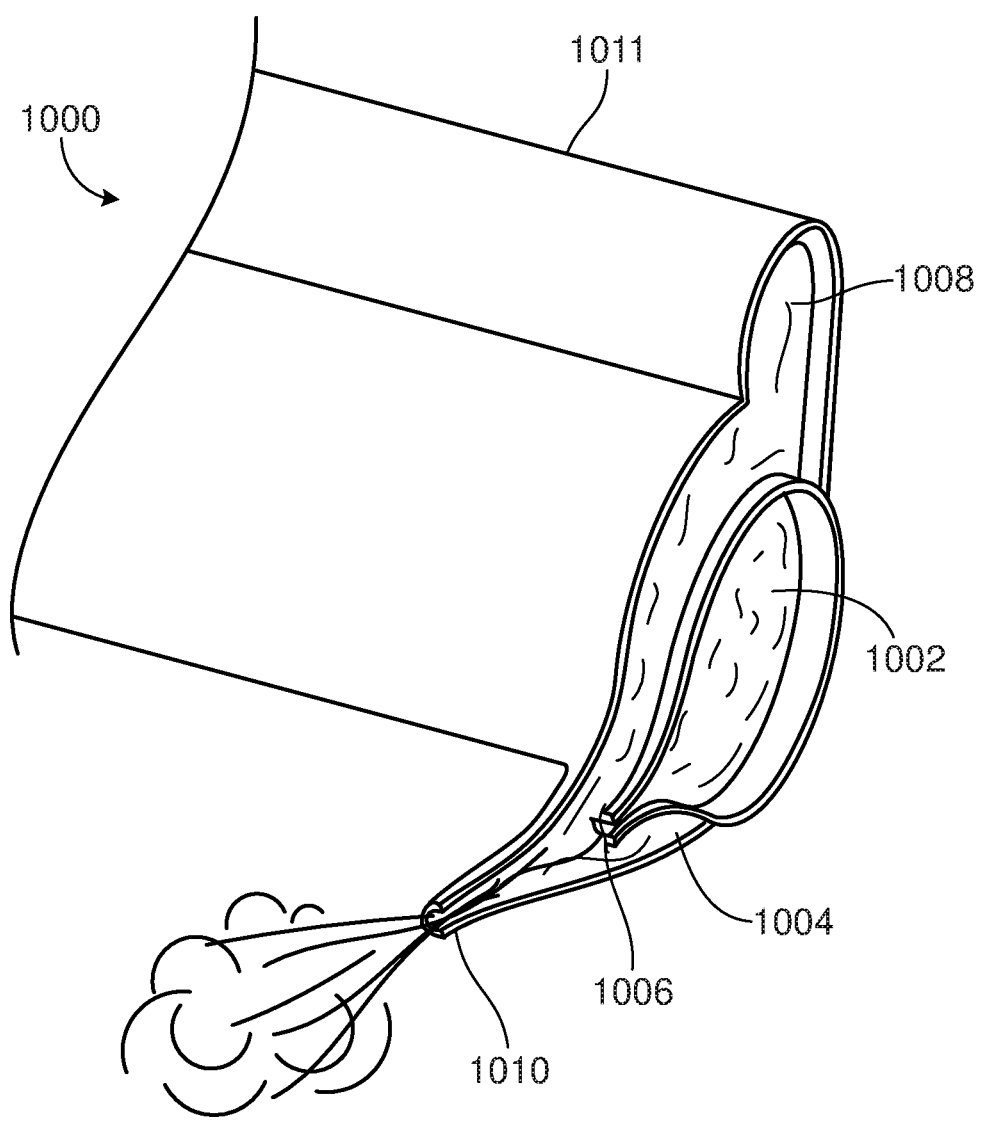
FIG. 9 is a cross-sectional view of a jet aeration mixer according to an alternate embodiment.

FIGS. 8 and 9 show two types of nozzle configurations that are designed to mix a gas and a liquid stream and eject a high velocity jet. These nozzles are configured somewhat differently from the eddy jet mixer shown in FIG. 7 but function in a similar manner. In the system 900 shown in FIG. 8, a primary or motive fluid is directed through a liquid line 902 to inner nozzles 904 through which the liquid travels at high velocity into a mixing area 906. A second fluid, e.g., a gas, such as compressed air, nitrogen or carbon dioxide, or a liquid, enters the mixing area through a second line 908 and entrained in the motive fluid entering the mixing area 906 through the inner nozzles. In some instances the second fluid is nitrogen or carbon dioxide so as to reduce oxidation of the enzyme. The combined flow from the two lines is jetted into the mixing vessel through the outer nozzles 910. If the second fluid is a gas, tiny bubbles are entrained in the liquid in the mixture. Liquid is supplied to the liquid line 902 by a pump. Gas, if it is used, is provided by compressors. If a liquid is used as the second fluid, it can have the same velocity as the liquid entering through the liquid line 902, or a different velocity.

FIG. 9 shows an alternate nozzle design 1000, in which outer nozzles 1010 (of which only one is shown) are positioned along the length of an elongated member 1011 that includes a liquid line 1002 that is positioned parallel to a second line 1008. Each nozzle includes a single outer nozzle 1010 and a single inner nozzle 1004. Mixing of the motive liquid with the second fluid proceeds in the same manner as in the system 900 described above.

In some embodiments, the jet nozzles are arranged to cause the contents of the tank to both revolve and rotate in a toroidal, rolling donut configuration around a central vertical axis of the vessel. Flow around the surface of the toroid is drawn down the vessel center, along the floor, up the walls and back to the center, creating a rolling helix pattern, which sweeps the center and prevents solids from settling. The toroidal pattern is also effective in moving floating solids to the vessel center where they are pulled to the bottom and become homogenous with the vessel contents. The result is a continuous helical flow pattern, which minimizes dead spots in the vessel contents.

Backflushing

In some instances, the jet nozzles described herein can become plugged, which may cause efficiency and cost effectiveness to be reduced. Plugging of the nozzles may be removed by reversing flow of the motive liquid through the nozzle.

Other Mixing Systems
Low Speed Agitators

Figure 10:
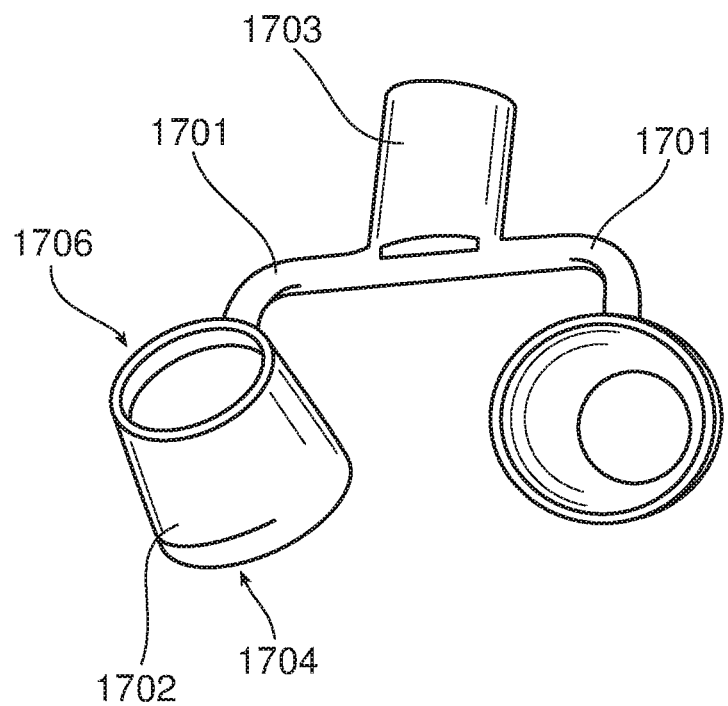
FIGS. 10 and 10A are perspective views of two embodiments of mixing heads used in a mixer according to an alternate embodiment.
Figure 10A:
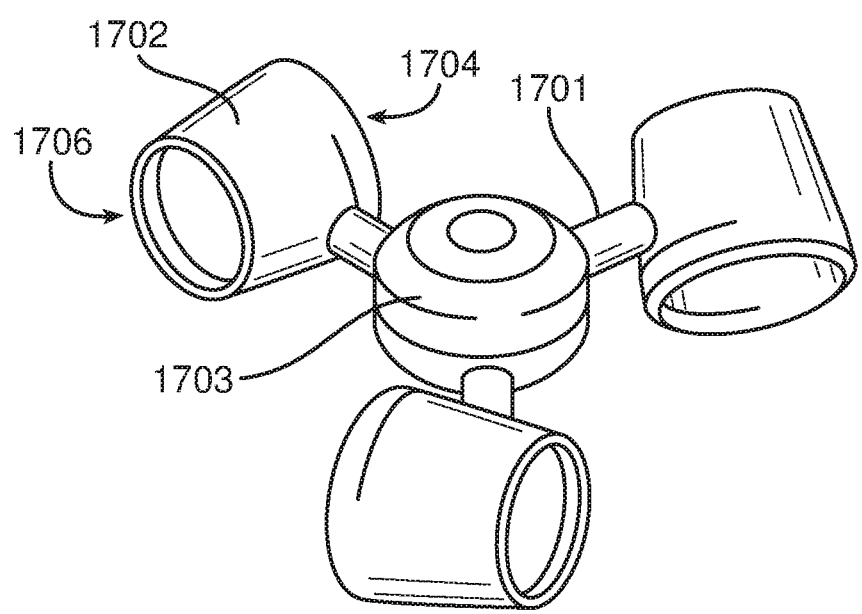

FIGS. 10 and 10A illustrate agitators configured to be mounted on a shaft (not shown) for rotational mixing at relatively low speeds. The agitators may include, for example, two mixing elements 1702 (FIG. 10), or three mixing elements (FIG. 10A), mounted on support arms 1701 about a central mounting hub 1703 that is disposed to receive a shaft.

The mixing elements 1702 are in the form of truncated cones, each of which has a first end 1704 and a second end 1706. The first end has a cross-section greater than the cross-section of the second end. The mixing elements are positioned such that the central axes of the mixing elements are disposed at an angle relative to a plane of rotation of the mixing elements.

The agitator is rotated in a direction so that liquid flows in through the first end 1704 and out through the second end 1706 at a higher velocity, creating dynamic flow conditions by generating turbulent flow at the tapered end of each mixing element. The angulation of the mixing elements relative to the plane of rotation tends to cause a continuous closed circular flow which in the vicinity of an adjacent vessel wall flows upwardly and in the central part of the vessel flows downwardly coaxially to the mixer shaft where it passes through the intermediate spaces between the support arms 1701. The intensity of this circular flow depends on the magnitude of the angle.

Mixers of this type are available commercially from Inotec under the tradename Visco-Jet™.

Materials
Medium

Bioprocessing, e.g., fermentation, is generally conducted in an aqueous growth medium, which can contain a nitrogen source or other nutrient source, e.g., urea, along with vitamins and trace minerals and metals. It is generally preferable that the growth medium be sterile, or at least have a low microbial load, e.g., bacterial count. Sterilization of the growth medium may be accomplished in any desired manner. However, in preferred implementations, sterilization is accomplished by irradiating the growth medium or the individual components of the growth medium prior to mixing. The dosage of radiation is generally as low as possible while still obtaining adequate results, in order to minimize energy consumption and resulting cost. For example, in many instances, the growth medium itself or components of the growth medium can be treated with a radiation dose of less than 5 Mrad, such as less than 4, 3, 2, or 1 Mrad. In specific instances, the growth medium is treated with a dose of between about 1 and 3 Mrad.

If the pH of the vessel contents is too low, this may tend to inhibit fermentation with some microorganisms, such as *Pichia stipitus*. Accordingly, it is in some cases desirable to add base and/or a buffer, before or during fermentation, to bring up the pH of the solution. For example, sodium hydroxide or lime can be added to the fermentation medium to elevate the pH of the medium to a range that is optimum for the microorganism utilized.

An example of a bioprocessing medium has the following concentrations of components:

| Yeast nitrogen base | 1.7 g/L |
|---|---|
| Urea | 2.27 g/L |
| Peptone | 6.56 g/L |
| Tween ® 80 surfactant | 10 g/L |

Microorganisms

Bioprocesses can utilize various microorganisms.

The microorganism may be a cell, e.g., a eukaryotic or prokaryotic cell. Eukaryotic cells include animal (e.g., mammalian) cells, plant cells, fungal cells, glaucophytes, haptophytes, cryptomonads, and amoeboid protists, e.g., amoebozoans and foraminifera. Prokaryotic cells include bacteria and archaea.

The microorganism can be a natural microorganism and/or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized. The microorganism can be an aerobe or an anaerobe. The microorganism can be a homofermentative microorganism (produces a single or a substantially single end product). The microorganism can be a homoacetogenic microorganism, a homolactic microorganism, a propionic acid bacterium, a butyric acid bacterium, a succinic acid bacterium or a 3-hydroxypropionic acid bacterium. The microorganism can be of a genus selected from the group consisting of *Clostridium, Lactobacillus, Moorella, Thermoanaerobacter, Proprionibacterium, Proionispera, Anaerobiospirillum,* and *Bacteriods*. In specific instances, the microorganism can be *Clostridium formicoaceticum, Clostridium butyricum, Moorella thermoacetica, Thermoanearobacter kivui, Lactobacillus delbrukii, Propionibacterium acidipropionici, Propionispera arboris, Anaerobiospirillum succiniproducens, Bacteriodes amylophilus,* or *Bacteriodes ruminicola*. For example, the microorganism can be a recombinant microorganism engineered to produce a desired product, such as recombinant *Escherichia coli* transformed with one or more genes capable of encoding proteins that direct the production of the desired product (see, e.g., U.S. Pat. No. 6,852,517, issued Feb. 8, 2005).

Enzymes

Enzymes, such as cellobiases and cellulases, are used in some bioprocesses.

Cellobiases include a cellobiase from *Aspergillus niger* sold under the tradename NOVOZYME 188™.

A cellulase may be of fungal or bacterial origin. Cellulases include those from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Enzyme complexes may be utilized, such as those available from Genencore under the tradename ACCELLERASE®, for example, Accellerase® 1500 enzyme complex. Accellerase 1500 enzyme complex contains multiple enzyme activities, mainly exoglucanase, endoglucanase (2200-2800 CMC U/g), hemi-cellulase, and beta-glucosidase (525-775 pNPG U/g), and has a pH of 4.6 to 5.0. The endoglucanase activity of the enzyme complex is expressed in carboxymethylcellulose activity units (CMC U), while the beta-glucosidase activity is reported in pNP-glucoside activity units (pNPG U). In one embodiment, a blend of Accellerase® 1500 enzyme complex and NOVOZYME™ 188 cellobiase is used.

Surfactants

The addition of surfactants can enhance the rate of some bioprocesses. Examples of surfactants include non-ionic surfactants, such as a Tween® 20 or Tween® 80 polyethylene glycol surfactants, ionic surfactants, or amphoteric surfactants. Other suitable surfactants include octylphenol ethoxylates such as the TRITON™ X series nonionic surfactants commercially available from Dow Chemical. A surfactant can also be added to keep a product that is being produced in solution, particularly in high concentration solutions.

Other Embodiments

A number of embodiments have been described. Nevertheless, it will be understood that various modifications may be made without departing from the spirit and scope of the disclosure.

For example, For example, the jet mixers described herein can be used in any desired combination, and/or in combination with other types of mixers. While a single jet mixer is shown in FIG. 1, a plurality of jet mixers can be used, e.g., as shown in FIG. 11, or a jet mixer could be used in combination with a different type of mixer, e.g., a marine impeller mixer.

The jet mixer(s) may be mounted in any desired position within the vessel. With regard to shaft-mounted jet mixers such as the one shown in FIG. 1, the shaft may be collinear with the center axis of the vessel, or may be offset therefrom, e.g., as shown in FIG. 11. For example, if desired the vessel may be provided with a centrally mounted mixer of a different type, e.g., a marine impeller or Rushton impeller, and a jet mixer may be mounted in another area of the vessel either offset from the center axis or on the center axis. In the latter case one mixer can extend from the top of the vessel while the other extends upward from the floor of the vessel.

In any of the jet mixing systems described herein, the flow of fluid (liquid and/or gas) through the jet mixer can be continuous or pulsed, or a combination of periods of continuous flow with intervals of pulsed flow. When the flow is pulsed, pulsing can be regular or irregular. In the latter case, the motor that drives the fluid flow can be programmed, for example to provide pulsed flow at intervals to prevent mixing from becoming "stuck." The frequency of pulsed flow can be, for example, from about 0.5 Hz to about 10 Hz, e.g., about 0.5 Hz, 0.75 Hz, 1.0 Hz, 2.0 Hz, 5 Hz, or 10 Hz. Pulsed flow can be provided by turning the motor on and off, and/or by providing a flow diverter that interrupts flow of the fluid.

The bioreactors described herein, or portions thereof, can be mobile, for example as described in U.S. Ser. No. 12/374,549, the full disclosure of which is incorporated herein by reference.

Accordingly, other embodiments are within the scope of the following claims.

What is claimed is:

1. A bioreactor comprising:
   a vessel,
   a jet mixing system comprising a plurality of jet flow agitators disposed in the vessel, each jet flow agitator comprising a shaft, a shroud surrounding the shaft, the shaft having a bore and a plurality of orifices in communication with the bore, and an impeller mounted on the shaft within the shroud, and
   a gas delivery system configured to supply a process gas to the vessel through the bore such that the gas exits the orifices,
   wherein the vessel includes a vent, and the gas delivery system includes a source of oxygen in communication with the vessel, an oxygen monitor configured to monitor the oxygen content of a liquid in the vessel, and a controller configured to adjust the oxygen content of the liquid, using the vent and oxygen source, in response to input from the oxygen monitor.

2. The bioreactor of claim 1 further comprising a plurality of sensors.

3. The bioreactor of claim 2 further comprising a process controller configured to receive input from the sensors.

4. The bioreactor of claim 1 further comprising a temperature control system configured to regulate temperature in the vessel.

5. The bioreactor of claim 1 further comprising a concentration monitor configured to monitor the concentration of a product in the liquid in the vessel, and a controller configured to stop a bioprocess taking place within the vessel based on input received from the concentration monitor.

6. The bioreactor of claim 1 wherein the jet mixing system further comprises a jet aeration mixer, or a suction chamber jet mixer.

7. The bioreactor of claim 1 further comprising delivery devices configured to deliver to the vessel a medium, microorganisms or cells, and/or other materials used in a bioprocess.

8. The bioreactor of claim 1 wherein the vessel includes an outlet through which effluent can be collected.

9. The bioreactor of claim 1 wherein the jet mixing system is configured to limit any increase in the overall temperature of a fluid medium in the vessel to less than 5 degrees C. over the course of mixing.

10. The bioreactor of claim 1 wherein the vessel is formed of glass and/or stainless steel.

11. The bioreactor of claim 1 wherein the vessel is jacketed.

12. The bioreactor of claim 1 wherein the vessel includes a port through which the contents of the vessel can be harvested or sampled.

13. The bioreactor of claim 2 wherein said sensors include a foam sensor, a dissolved oxygen sensor, and a pH sensor.

14. The bioreactor of claim 1 wherein the jet mixing system includes a torque controller.

15. The bioreactor of claim 1 wherein the jet mixing system is configured for pulsating flow.

16. The bioreactor of claim 15 wherein the jet mixing system comprises a flow diverter.

\* \* \* \* \*